(12) United States Patent
Cassone et al.

(10) Patent No.: US 8,445,484 B2
(45) Date of Patent: May 21, 2013

(54) BICYCLIC PEPTIDOMIMETIC INHIBITORS OF ASPARTYL-PROTEASES FOR THE TREATMENT OF INFECTIOUS DISEASES

(75) Inventors: Antonio Cassone, Rome (IT); Flavia De Bernardis, Rome (IT); Enrico Garaci, Rome (IT); Andrea Trabocchi, Florence (IT); Antonio Guarna, Sesto Fiorentino (IT)

(73) Assignees: Istituto Superiore di Sanita', Rome (IT); Universita' Degli Studi di Firenze, Florence (IT)

( * ) Notice: Subject to any disclaimer, the term of this patent is extended or adjusted under 35 U.S.C. 154(b) by 44 days.

(21) Appl. No.: 13/130,666

(22) PCT Filed: Nov. 24, 2009

(86) PCT No.: PCT/EP2009/065728
§ 371 (c)(1),
(2), (4) Date: May 23, 2011

(87) PCT Pub. No.: WO2010/060904
PCT Pub. Date: Jun. 3, 2010

(65) Prior Publication Data
US 2011/0237577 A1 Sep. 29, 2011

(30) Foreign Application Priority Data

Nov. 25, 2008 (EP) .................................... 08169901

(51) Int. Cl.
*C07D 498/08* (2006.01)
*A61K 31/553* (2006.01)
(52) U.S. Cl.
USPC ...................................... 514/230.5; 544/105
(58) Field of Classification Search
USPC ...................................... 544/105; 514/230.5
See application file for complete search history.

(56) References Cited

U.S. PATENT DOCUMENTS
2006/0258648 A1   11/2006   Bezencon et al.

FOREIGN PATENT DOCUMENTS
WO   WO04000324   12/2003

OTHER PUBLICATIONS

The Merck Manual of Medical Information—Home Edition, Section 17. Infections, Chapter 184 on the web site http:llwww.merck.comlmrkshared/mmanual_homelsec171184.jsp, downloaded on Nov. 26, 2003.*
Notification of Transmittal of the International Search Report and the Written Opinion of the International Searching Authority, or the Declaration of International Application No. PCT/EP2009/065728 Mailed Aug. 2, 2010.
Fabrizio Machetti; Parallel Synthesis of an Amide Library Based on the 6,8-Dioxa-3-Azabicyclo[3.2.1] Octane Scaffold by Direct Aminolysis of Methyl Esters; Journal of Combinatorial Chemistry; 2007; 9; 454-461.
Fabrizio Machetti; Neat Reaction of Carboxylic Acid Methyl Esters and Amines for Efficient Parallel Synthesis of Scaffold Amide Libraries; C.R. Chimie 6 (2003) 631-633.
Tacconelli; Candidiasis and HIV-Protease Inhibitors: The Expected and the Unexpected; Curr. Med. Chem.-Immun., Endoc. & Memb. Agents, 2004, 4, 49-59.
Antonio Guarna et al.; Synthesis and Reactivity of Bicycles Derived From Tartaric Acid and α-Amino Acids; A Novel Class of Conformationally Constrained Dipeptide Isosteres Based Upon Enantiopure 3-Aza-6,8-Dioxabicyclo[3.2.1] Octane-7-Carboxylic Acid; J. Org. Chem. 1999, 64, 7347-7364.

* cited by examiner

*Primary Examiner* — Kahsay T Habte
(74) *Attorney, Agent, or Firm* — Abelman, Frayne & Schwab

(57) ABSTRACT

The present invention refers to 3-aza-bicyclo [3.2.1] octane derivatives of general formula (I) their preparation, use and pharmaceutical compositions useful in the treatment of pathologies associated with microbial pathogens expressing aspartylprotease activity.

11 Claims, 1 Drawing Sheet

FIGURE 1
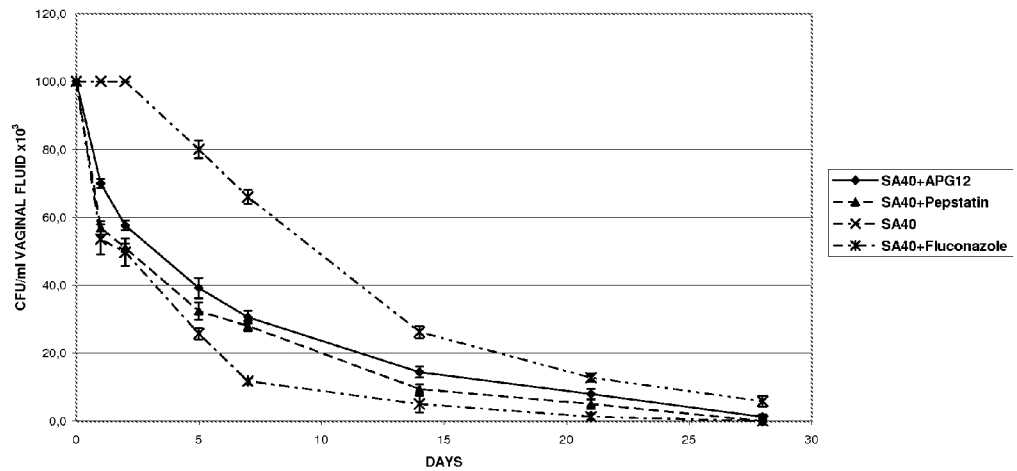
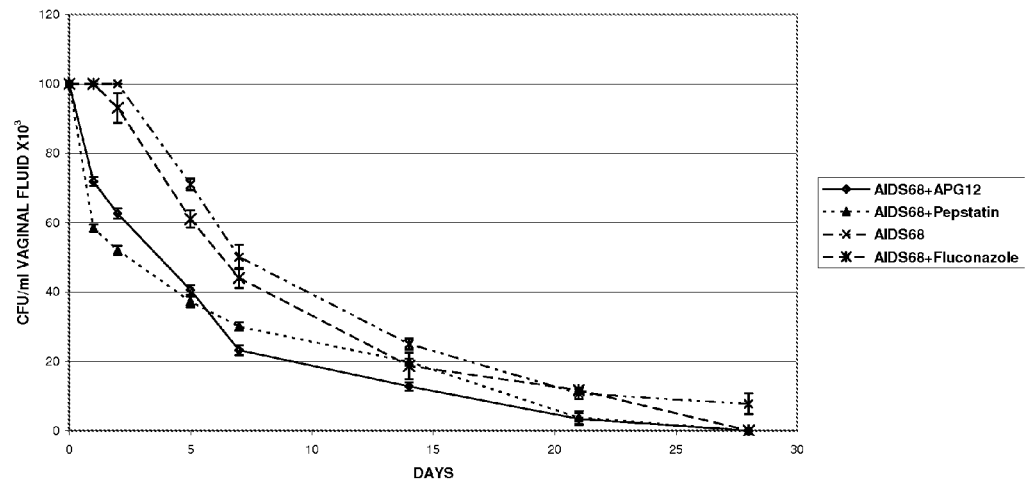
FIGURE 2

BICYCLIC PEPTIDOMIMETIC INHIBITORS OF ASPARTYL-PROTEASES FOR THE TREATMENT OF INFECTIOUS DISEASES

CROSS-REFERENCE TO RELATED APPLICATIONS:

This application is a §371 National Phase of PCT/EP2009/065728, filed 24 Nov. 2009, which claims priority from European Application 08169901.9, filed 25 Nov. 2008.

FIELD OF THE INVENTION

The present invention refers to 3-aza-bicyclo[3.2.1]octane derivatives of general formula (I) useful in the treatment of infectious diseases and particularly pathologies caused by microbial pathogens expressing aspartyl-protease activity. Specifically, the invention refers to compounds of general formula (I), and their metabolites, as *Candida albicans* SAP2 inhibitors for treating fungus infections, as HIV protease inhibitors for treating HIV infections, or as plasmepsines or histo-aspartyl protease (HAP) inhibitors for treating malaria.

STATE OF THE ART

Aspartyl proteases are widely distributed in many organisms and tissues with different physiological and functional properties, and contain two aspartyl residues at the active site, one protonated and the other not, which work together as general acid-base catalysis. A water molecule bound between the two aspartate residues is believed to be the nucleophile for the amide bond hydrolysis, and it is activated by the deprotonated catalytic aspartic acid residue. To catalyse peptide hydrolysis, the two aspartic residues must be close enough in the tertiary structure of the molecule. Most of the aspartic proteases belong to the pepsin family, including digestive enzyme such as pepsin and chimotrypsin, as well as lysosomal cathepsins D and processing enzymes such as renin and certain fungal proteases (the *Candida albicans* SAPs, penicillopepsin etc). A second family comprises viral proteases such as the HIV, also called retropepsin. The active site of aspartic proteases does not in general contain groups that are sufficiently nucleophilic to be chemically modified by a selective irreversible inhibitor. Thus, most of the aspartic protease inhibitors developed to date binds to their target enzyme through non covalent interactions. These compounds are therefore reversible inhibitors and an effective inhibition results when the enzyme shows higher affinity for the inhibitor than for its natural substrate (Tacconelli, E. et al. *Curr. Med. Chem.* 2004, 4, 49).

It has been proposed that stable structures which resemble the transition state of an enzyme-catalysed reaction should bind the enzyme more tightly than the substrate. As a consequence, an approach that has been very successful for the design of efficient aspartyl protease inhibitors is based on the incorporation of a transition state isostere into a peptidomimetic structure.

*Candida albicans* is an opportunistic fungal pathogen that causes severe systemic infections especially in immunodeficient individuals. Although a certain number of antifungal agents are available, the need for new drugs against *C. albicans* is escalating due to both the widespread occurrence of mucosal and systemic infections caused by *Candida*, and the development of resistance against available drugs (Shao, P.-L. et al. *Int. J. Antimicrob. Agents* 2007, 30, 487). In fact, despite drug availability, *Candida albicans* ranks as a highly incident cause of morbidity, cost of hospitalization and mortality (Pfaller M A & D: J: Diekema. Epidemiology of invasive Candidiasis: a persistent public health Problem. Clin.Microbiol.Rev. 2007; 20:133-163). Although the ability to cause disease is likely a complex process involving multiple interactions between *Candida* and the host, Secreted Aspartyl Proteases (SAPs) activity appears to be a major virulence factor and therefore offers a potential target for drug intervention in infections. The *Candida* strains express at least nine distinct genes (SAP1-9) during the course of the same disease but to different stages of infection, indicating that the different SAPs have different functions (Schaller, M. et al. *J. Invest. Dermatol.* 2000, 114, 712); particularly, among them SAP2 is one of the most expressed enzymes implicated in host persistent colonization and invasion.

Other strong evidence of the need of inhibitors of aspartyl protease activity are due to the following aspects:

Immunodeficient patients suffering of infections caused by *Candida albicans* can develop systemic candidiasis and also resistance to common therapeutics.

HIV and HTVL viruses rely upon their aspartyl proteases for viral maturation.

*Plasmodium falciparum* uses plasmepsines I and II for processing hemoglobin.

Recently, the inhibitory activity of HIV protease inhibitors (HIV-PI) against pathogenic microorganisms in which aspartyl proteases play a key role has been demonstrated (Tacconelli et al., *Curr. Med. Chem.*, 2004, 4, 49). Particularly, HIV-PI show micromolar activity towards aspartyl proteases of both *Candida albicans* (Cassone et al., *J. Infect. Dis.*, 1999, 180, 448), and malaria plasmepsines II and IV (Andrews et al., *Antimicrob. Agents Chemother.* 2006, 639). Such results are in agreement with the flexibility of these molecules and some structural analogy between aspartyl proteases of HIV-1 and SAP2 of *Candida albicans*.

Thus, new compounds having inhibitory activity towards aspartyl proteases can act as *Candida albicans* SAP2 inhibitors for treating fungus infections, as HIV protease inhibitors for treating HIV infections, as plasmepsines or histo-aspartyl protease (HAP) inhibitors for treating malaria.

Compounds of formula (I)

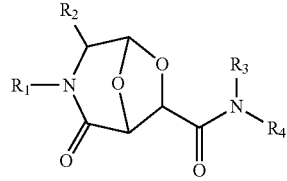

(I)

wherein:

R1 is chosen in the group consisting of H, benzyl, p-methoxybenzyl, benzhydryl; preferably benzyl;

R2 is a chosen in the group consisting of H, alkyl, aryl, alkylaryl; preferably H, benzyl, methyl, isobutyl.

R3 and R4 are independently chosen in the group consisting of H, alkyl, alkenyl, alkynyl, cycloalkyl, alkylaryl, aryl, hydroxyalkyl, alkoxyalkyl, alkoxycarbonyl, —CH(α-amino acid side chain)CH2OH; preferably H, hydroxyethyl, propargyl, —CH(Leu side chain)CH2OH;

R3 and R4 together with the nitrogen atom they are bonded to can form a cycle, eventually substituted; preferably piperidine, 4-hydroxyethyl-piperazine, 4-carboethoxy-piperazine, morpholine; including all the possible combinations of stereoisomers;

are known.

Their preparation has been reported in *J. Org. Chem.* 1999, 64, 7347; *J. Org. Chem.* 2002, 67, 7483; *Bioorg. Med. Chem.* 2001, 9, 1625; *Eur. J. Org. Chem.* 2002, 873; *J. Org. Chem.* 2002, 67, 7483; *C. R. Chimie* 2003, 631; *J. Comb. Chem.* 2007, 9, 454.

Their use in pharmaceutical compositions for the treatment of pathologies related to deficit of neurotrofines activity has been described in WO2004/000324.

Thus, aim of the present invention is to furnish alternative compounds for the preparation of medicaments for the treatment of pathologies related to aspartyl protease activity, and specifically of SAP2, and more specifically for the treatment of pharmaco-resistant systemic infections of *Candida albicans* in immunodepressed patients.

BRIEF DESCRIPTION OF THE DRAWINGS

FIG. 1—Vaginal infection with *C. albicans* SA40 in rats intravaginally treated with APG12 after challenge (1, 24, 48 hrs)

FIG. 2—Vaginal infection with *C. albicans* AIDS 68 in rats intravaginally treated with APG12 after challenge (1, 24, 48 hrs)

DETAILED DESCRIPTION OF THE INVENTION

The present invention refers to compounds of formula (I)

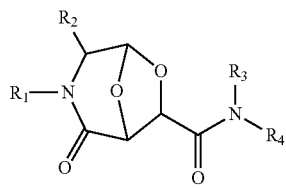

(I)

wherein:

R1 is a —CH(R)COR5;

R is a α-amino acid side chain, preferably said α-amino acid is chosen among the group consisting of Gly, Leu, Val, Ile, Ala, Phe, Phg, Nle, Nva;

R2 is H, alkyl, aryl, alkylaryl, preferably H, benzyl, methyl, isobutyl;

R3 and R4 are independently chosen in the group consisting of H, alkyl, alkenyl, alkynyl, cycloalkyl, alkylaryl, aryl, hydroxyalkyl, alkoxyalkyl, alkoxycarbonyl, —CH(α-amino acid side chain)CH2OH; preferably H, hydroxyethyl, propargyl, —CH(Leu side chain)CH2OH;

R3 and R4 together with the nitrogen atom they are bonded to can form a 5 to 8 membered cycle, eventually substituted; preferably piperidine, 4-hydroxyethyl-piperazine, 4-carboethoxy-piperazine, 4-benzyl-piperazine, 4-phenethyl-piperazine, morpholine;

R5 is chosen in the group consisting of —Oalkyl, —Oaryl, —NHalkyl, NHaryl, amino acid, peptide; preferably —OCH3, NHCH2CH(OH)CH2CONHBu;

including all the possible combinations of stereoisomers.

Surprisingly, it has been discovered that compounds of formula (I)

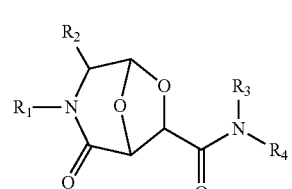

(I)

wherein:

R1 is chosen in the group consisting of benzyl, phenyl, —CH(R)COR5; preferably benzyl, —CH(R)COR5;

R is a α-amino acid side chain; preferably said α-amino acid is chosen among the group consisting of Gly, Leu, Val, Ile, Ala, Phe, Phg, Nle, Nva;

R2 is H, alkyl, aryl, alkylaryl, preferably H, benzyl, methyl, isobutyl;

R3 and R4 are independently chosen in the group consisting of H, alkyl, alkenyl, alkynyl, cycloalkyl, alkylaryl, aryl, hydroxyalkyl, alkoxyalkyl, alkoxycarbonyl, —CH(α-amino acid side chain)CH2OH; preferably H, hydroxyethyl, propargyl, —CH(Leu side chain)CH2OH;

R3 and R4 together with the nitrogen atom they are bonded to can form a 5 to 8 membered cycle, eventually substituted; preferably piperidine, 4-hydroxyethyl-piperazine, 4-carboethoxy-piperazine;

R5 is chosen in the group consisting of —Oalkyl, —Oaryl, —NHalkyl, NHaryl, α-amino acid, peptide; preferably —OCH3, NHCH2CH(OH)CH2CONHBu;

including all the possible combinations of stereoisomers;

are potent inhibitors both in vitro and in vivo of SAP2, thus they can be used for the preparation of medicaments for treating infectious diseases, preferably related to *Candida albicans*, HIV, HTVL, *Plasodium falciparum*.

An aspect of the present invention relates to pharmaceutical compositions containing at least a compound of formula (I), wherein R1 is —CH(α-amino acid side chain)COR5; preferably such α-amino acid is chosen in the group consisting of Gly, Leu, Val, Ile, Ala, Phe, Phg, Nle, Nva; and at least another pharmaceutically acceptable ingredient, excipient, carrier or diluent.

According to the invention:

Alkyl means linear or branched radical chain, such as: methyl, ethyl, propyl, isopropyl, butyl, pentyl, hesyl, heptyl, octyl, ethenyl, propenyl, butenyl, isobutenyl, acetylenyl, propynyl, butynyl, etc. . . . ;

Aryl means aromatic or heteroaromatic ring containing heteroatoms like N, O, S. Amino acid side chain means diverse substitution as a side chain bound to an "amino acid". The term "amino acid" includes every natural α-amino acids of the L or D series having as "side chain": —H for glycine; —CH3 for alanine; —CH(CH3)2 for valine; —CH2CH(CH3)2 for leucine; —CH(CH3)CH2CH3 for isoleucine; —CH2OH for serine; —CH(OH)CH3 for threonine; —CH2SH for cysteine; —CH2CH2SCH3 for methionine; —CH2-(fenil) for phenylalanine; —CH2-(fenil)-OH for tyrosine; —CH2-(indole) for tryptophan; —CH2COOH for aspartic acid; —CH2C(O)(NH2) for asparagine; —CH2CH2COOH for glutamic acid; —CH2CH2C(O)NH2 for glutamine; —CH2CH2CH2-N(H)C(NH2)NH for arginine; —CH2-(imidazole) for hystidine; —CH2(CH2)3NH2 for lysine, comprising the same side chains of amino acids bearing suitable protecting groups. Moreover, the term "amino acid" includes non natural amino acids, such as ornitine (Orn), norleucine (Nle), norvaline (NVa), β-alanine, L or D α-phenylglycine (Phg), diaminopropionic acid, diaminobutyric acid, aminohydroxybutyric acid, and other well known in the state of the art of peptide chemistry.

Scheme 1 summarizes the synthetic preparation of compounds of formula (I) as described above, wherein R1 is —CH(R)COR5, R is a α-amino acid side chain, from commercially available or easily synthesizable α-amino-acid derivatives (II).

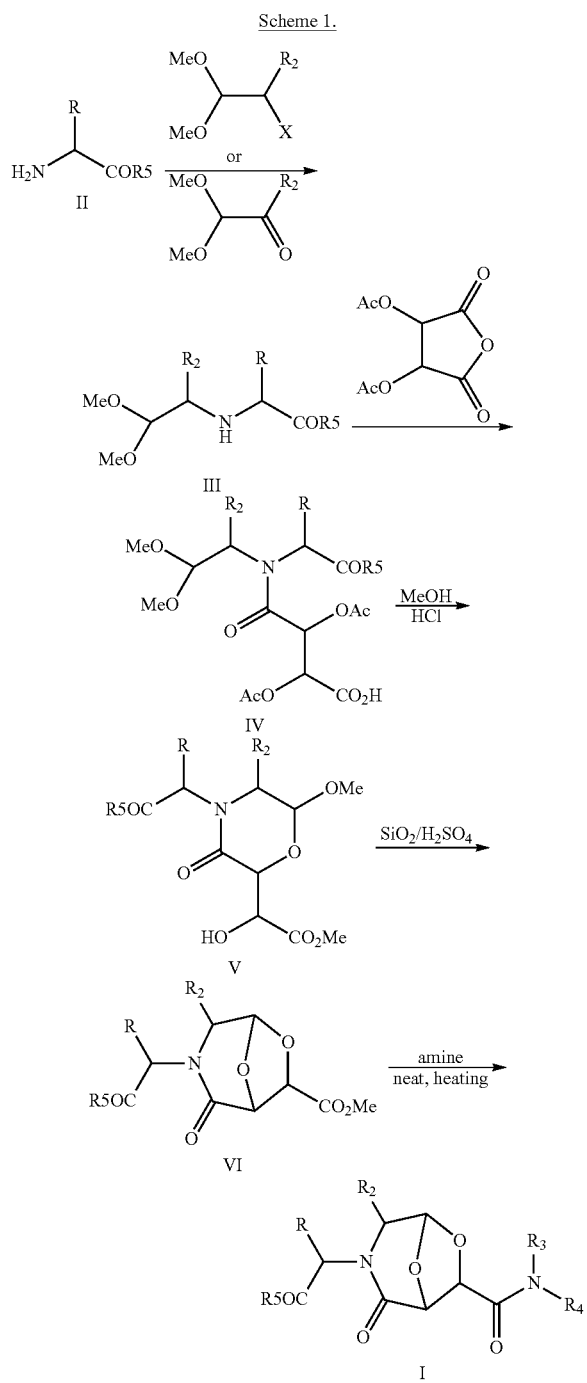

Reductive alkylation of the amino acid derivative (II) with a commercially available or easily synthesisable dicarbonyl derivative, for example dimethoxy-acetaldehyde, in a protic solvent, preferably methanol, using a reducing agent, preferably H2 and a catalyst, preferably Pd/C, affords the secondary amine (III) after stirring at ambient temperature, preferably 16 h at 25° C. Alternatively, compound (II) is heated with a commercially available or easily synthesisable acetal derivative containing a good leaving group (X in Scheme 1), for example bromoacetaldehyde dimethylacetal, preferably at 120° C., in a polar solvent, preferably DMF, in the presence of a base, preferably NEt3, and in the presence of a catalyst, preferably KI. Amine (III) is successively converted into the amide (IV) through a coupling reaction with di-O-acetyl-tartaric anhydride. Treatment of crude (IV) with an acid in a polar solvent, preferably thionyl chloride in MeOH affords cyclic acetal (V) which is further heated in a non-polar solvent, preferably in refluxing toluene for 30 min, in the presence of an acid catalyst, preferably H2SO4 over silica gel, to yield (VI).

The synthesis of amides (I) is accomplished without using activating agents, by heating the methyl ester (VI) in the presence of the neat amine, preferably at 60° C. for 18 h.

The following examples are reported to give a non-limiting illustration of the present invention.

EXPERIMENTAL DETAILS

Example 1

(2S)-4-Methyl-2-[(1R,5S,7S)-2-oxo-7-(piperidine-1-carbonyl)-6,8-dioxa-3-aza-bicyclo[3.2.1]oct-3-yl]-pentanoic acid methyl ester [compound formula (I), where R1=—CH(Leu side chain)COOCH3, R2=H, R3 and R4=—CH2(CH2)3CH2-]

A solution containing L-leucine methyl ester hydrochloride (2.9 g, 16 mmol), 2-bromo-1,1-dimethoxy ethane (1.9 ml, 2.7 g, 16 mmol), NEt3 (6.7 ml, 48 mmol) and a catalytic amount of KI in DMF (190 ml) was stirred at 120° C. for 3 days. The reaction mixture was concentrated under reduced pressure, diluted with water and extracted with DCM. The organic layer was then washed with brine, dried over Na2SO4 and evaporated. The crude product was purified by column chromatography (silica gel, EtOAc/P.E. 1:1) to afford compound of formula (III), where R=Leu side chain, as a yellow oil (1.2 g, 32% yield).

$[\alpha]_D^{24}$ −3.32 (c 1.0, CHCl$_3$); $^1$H-NMR (CDCl3, 200 MHz): δ 4.38 (t, J=6 Hz, 1H), 3.65 (s, 3H), 3.30 (s, 3H), 3.29 (s, 3H), 3.24 (t, J=6 Hz, 1H), 2.68 (dd, J$_1$=J$_2$=6 Hz, 1H), 2.52 (dd, J$_1$=J$_2$=6 Hz, 1H), 1.71-1.55 (m, 2H), 1.44-1.37 (m, 2H), 0.86 (d, J=4 Hz, 3H), 0.83 (d, J=4 Hz, 3H); $^{13}$C-NMR (CDCl3, 200 MHz): δ 175.9 (s), 103.6 (d), 59.9 (d), 54.0 (q), 53.1 (q), 51.7 (q), 49.3 (t), 42.8 (t), 25.0 (d), 22.8 (q), 22.5 (q); MS m/z 233 (0.5), 202 (7.2), 174 (33), 158 (14), 75 (100); IR (CHCl3) 2915, 1729, 1130, 1065 cm$^{-1}$; Anal. Calcd for C11H23NO4 (233.30): C, 56.63; H, 9.94; N, 6.00. Found: C, 57.49; H, 9.90; N, 6.24.

To a suspension of (S,S)-2,3-di-O-acetyl-tartaric anhydride (1 g, 4.7 mmol) in dry DCM (4.5 ml) was added, at 0° C. and under a nitrogen atmosphere, a solution of compound of formula (III), where R=Leu side chain, (1 g, 4.7 mmol) in dry DCM (2.5 ml). The reaction mixture was stirred at room temperature overnight. After evaporation of the solvent, the crude product of formula (IV), where R=Leu side chain, was dissolved in MeOH (8 ml) and thionyl chloride (292 μl 4 mmol) was added dropwise at 0° C. The mixture was then allowed to reach 60° C. and stirred for 2 h. The solvent was removed and the crude compound of formula (V), where R=Leu side chain, was isolated as a yellow oil and used without further purification in the next step.

A solution of (V), where R=Leu side chain, (1.63 g, 4.7 mmol) in toluene (8 ml) was quickly added to a refluxing suspension of SiO2/H2SO4 (1 g) in toluene (12 ml). The mixture was allowed to react for 30 min, and then one-third of the solvent was distilled off. The hot reaction mixture was filtered through a pad of NaHCO3 and, after evaporation of the solvent, the crude product was purified by flash chromatography (silica gel, EtOAc/P.E. 1:2) affording (VI), where R=Leu side chain, as a white solid (730 mg, 50% yield over three steps).

$[\alpha]_D^{24}$ 22.0 (c 1.0, MeOH); $^1$H-NMR (CDCl3, 200 MHz): δ 5.88 (d, J=2 Hz, 1H), 5.09 (t, J=8 Hz, 1H), 4.87 (s, 1H), 4.59 (s, 1H), 3.72 (s, 3H), 3.64 (s, 3H), 3.50 (dd, $J_1$=12 Hz, $J_2$=2 Hz, 1H), 3.11 (dd, $J_1$=12 Hz, $J_2$=2 Hz, 1H), 1.67-1.60 (m, 2H), 1.46-1.32 (m, 1H), 0.88 (s, 3H), 0.84 (s, 3H); $^{13}$C-NMR (CDCl3, 200 MHz): δ 170.8 (s), 168.7 (s), 165.6 (s), 100.0 (d), 77.8 (d), 77.3 (d), 52.8 (d), 52.4 (q), 52.3 (q), 48.1 (t), 36.6 (t), 24.7 (d), 23.3 (q), 21.3 (q); MS m/z 315 (11), 256 (100), 240 (4); Anal. Calcd for C14H21NO7 (315.33): C, 53.33; H, 6.71; N, 4.44. Found: C, 52.99; H, 5.58; N, 4.79.

A solution containing (VI), where R=Leu side chain, (1 g, 3.2 mmol) and piperidine (6.3 ml, 63 mmol) was stirred at 60° C. overnight. The reaction mixture was then concentrated under reduced pressure, and the crude product was purified by column chromatography (silica gel, DCM/MeOH 20:1) to afford compound of formula (VII), where R=Leu side chain, R3 and R4=—CH2(CH2)3CH2- (corresponding to compound of formula (I), where R1=—CH(Leu side chain)COOCH3, R2=H, R3 and R4=—CH2(CH2)3CH2-), as a yellow oil (816 mg, 70% yield).

$[\alpha]_D^{22}$ 33.6 (c 1.0, CHCl$_3$); $^1$H-NMR (CDCl3, 200 MHz): (mixture of two rotamers) δ 5.79 (d, 1H, J=1.4 Hz), 5.06-4.94 (m, 1H), 5.02 (s, 1H), 4.82 (s, 1H, minor), 4.71 (s, 1H, major), 3.62 (s, 3H, minor), 3.61 (s, 3H, major), 3.55-3.20 (m, 5H), 3.09 (d, J=11.8 Hz, 1H), 1.67-1.34 (m, 9H), 0.86 (d, J=4.8 Hz, 3H), 0.84 (d, J=5.8 Hz, 3H); $^{13}$C-NMR (CDCl3, 200 MHz) (mixture of two rotamers): δ 171.1 (s, minor), 170.8 (s, major), 167.6 (s, minor), 166.8 (s, major), 164.9 (s, minor), 164.8 (s, major), 99.6 (d, major), 99.5 (d, minor), 78.0 (d), 76.4 (d), 52.7 (q), 52.4 (d, major), 52.2 (d, minor), 48.6 (t, major), 47.7 (t, minor), 46.4 (t), 43.5 (t), 36.7 (t, major), 35.8 (t, minor), 26.4 (t), 25.5 (t), 24.7 (d), 24.5 (t), 23.2 (q), 21.5 (q); MS m/z 368 (M+), 309 (21), 312 (100); IR (CHCl3) 2935, 1739, 1666 cm$^{-1}$. Anal. Calcd. for C18H29N3O6 (368.43): C, 58.68; H, 7.66; N, 7.60. Found: C, 57.06; H, 7.50; N, 8.32

Example 2

(2S)-2-[(1R,5S,7S)-7-(4-methyl-piperazine-1-carbonyl)-2-oxo-6,8-dioxa-3-aza-bicyclo[3.2.1]oct-3-yl]-4-methyl-pentanoic acid methyl ester [compound of formula (I), where R1=—CH(Leu side chain) COOCH3, R2=H, R3 and R4=—CH2CH2N(CH3) CH2CH2-]

Compound (I), where R1=—CH(Leu side chain) COOCH3, R2=H, R3 and R4=—CH2CH2N(CH3) CH2CH2- was prepared according to the procedure described for compound (I), where R1=—CH(Leu side chain) COOCH3, R2=H, R3 and R4=—CH2(CH2)3CH2-, starting from compound (VI), where R=Leu side chain, (150 mg, 0.48 mmol) and 1-methyl piperazine (1.06 ml, 9.5 mmol). Pure compound (I), where R1=—CH(Leu side chain)COOCH3, R2=H, R3 and R4=—CH2CH2N(CH3)CH2CH2-, (128 mg, 72% yield) was obtained as yellow oil.

$[\alpha]_D^{25}$ 28.1 (c 0.9, CHCl3); $^1$H-NMR (CDCl3, 200 MHz): δ 5.85 (s, 1H), 5.12 (s, 1H), 5.05 (t, J=8 Hz, 1H), 4.77 (s, 1H), 3.68 (s, 3H), 3.62-3.51 (m, 5H), 3.14 (d, J=12 Hz, 1H), 2.42-2.33 (m, 4H), 2.72 (s, 3H), 1.73-1.65 (m, 2H), 1.49-1.42 (m, 1H), 0.92 (d, J=6 Hz, 3H), 0.90 (d, J=4 Hz, 3H); $^{13}$C-NMR (CDCl3, 200 MHz): δ 170.8 (s), 166.8 (s), 165.0 (s), 99.7 (d), 78.0 (d), 76.4 (d), 55.0, 54.6 (t), 52.8 (q), 52.5 (d), 48.6 (t), 46.1 (q), 45.4 (t), 42.3 (t), 36.9 (t), 24.8 (d), 23.3 (q), 21.6 (q); MS m/z 383 (23), 352 (2.4), 324 (9), 99 (55), 70 (100); IR(CHCl3) 2866, 1738, 1670 cm$^{-1}$; Anal. Calcd. for C18H29N3O6 (383.44): C, 56.38; H, 7.62; N, 10.96. Found: C, 55.12; H, 6.88; N, 12.01.

Example 3

4'-Methyl-(2'S)-2'-[(1R,5S,7S)-7-(morpholine-4-carbonyl)-2-oxo-6,8-dioxa-3-aza-bicyclo[3.2.1]oct-3-yl]-pentanoic acid methyl ester [compound of formula (I), where R1=—CH(Leu side chain)COOCH3, R2=H, R3 and R4=—CH2CH2OCH2CH2-]

Compound of formula (I), where R1=—CH(Leu side chain)COOCH3, R2=H, R3 and R4=—CH2CH2OCH2CH2- was prepared according to the procedure described for compound of formula (I), where R1=—CH(Leu side chain)COOCH3, R2=H, R3 and R4=—CH2(CH2)3CH2-, starting from compound (VI), where R=Leu side chain, (100 mg, 0.32 mmol) and morpholine (0.55 ml, 6.3 mmol). Pure compound of formula (I), where R1=—CH(Leu side chain)COOCH3, R2=H, R3 and R4=—CH2CH2OCH2CH2- (95 mg, 65% yield) was obtained as a yellow oil.

$[\alpha]_D^{22}$ 29.0 (c 1.0, CHCl3); $^1$H-NMR (CDCl3, 200 MHz): δ 5.86 (d, J=2 Hz, 1H), 5.16 (s, 1H), 5.06 (dd, $J_1$=$J_2$=8 Hz, 1H), 4.76 (s, 1H), 3.70 (s, 3H), 3.67-3.52 (m, 9H), 3.15 (d, J=12 Hz, 1H), 1.75-1.67 (m, 2H), 1.53-1.43 (m, 1H), 0.94 (d, J=6 Hz, 3H), 0.92 (d, J=6 Hz, 3H); $^{13}$C-NMR (CDCl3, 200 MHz): δ 170.8 (s), 99.8 (d), 84.6 (d), 78.0 (d), 66.8 (t), 66.6 (t), 52.8 (q), 52.5 (d), 48.6 (t), 46.0 (t), 42.7 (t), 36.8 (t), 24.8 (d), 23.3 (q), 21.6 (q); MS m/z 370 (14), 311 (60), 283 (19), 168 (100); IR (CHCl3) 2932, 1735, 1668 cm$^{-1}$; Anal. Calcd for C17H26N2O7 (370.41): C, 55.13; H, 7.08; N, 7.56. Found: C, 54.27; H, 6.40; N, 7.22.

Example 4

(2S)-2-[(1R,5S,7S)-7-(4-benzyl-piperazine-1-carbonyl)-2-oxo-6,8-dioxa-3-aza-bicyclo[3.2.1]oct-3-yl]-4-methyl-pentanoic acid methyl ester [compound of formula (I), where R1=—CH(Leu side chain) COOCH3, R2=H, R3 and R4=—CH2CH2N(benzyl) CH2CH2-]

Compound of formula (I), where R1=—CH(Leu side chain)COOCH3, R2=H, R3 and R4=—CH2CH2N(benzyl) CH2CH2- was prepared according to the procedure described for compound of formula (I), where R1=—CH(Leu side chain)COOCH3, R2=H, R3 and R4=—CH2(CH2)3CH2-, starting from compound of formula (VI), where R=Leu side chain, (100 mg, 0.32 mmol) and 1-benzyl piperazine (1.1 ml, 6.3 mmol). Pure compound of formula (I), where R1=—CH (Leu side chain)COOCH3, R2=H, R3 and R4=—CH2CH2N (benzyl)CH2CH2- (106 mg, 72% yield) was obtained as a yellow oil.

$[\alpha]_D^{23}$ 20.1 (c 1.1, CHCl3); $^1$H-NMR (CDCl3, 200 MHz): δ 7.42-7.27 (m, 5H), 5.88 (s, 1H), 5.25-5.05 (m, 2H), 4.79 (s, 1H), 3.71 (s, 3H), 3.63-3.53 (m, 7H), 3.16 (d, J=11.6 Hz, 1H), 2.51-2.45 (m, 4H), 1.76-1.68 (m, 2H), 1.55-1.25 (m, 1H), 0.96 (d, J=5, 3H), 0.93 (d, J=6.2 Hz, 3H); $^{13}$C-NMR (CDCl3, 200 MHz): δ 170.8 (s), 166.8 (s), 165.0 (s), 129.1 (d), 128.3 (d), 127.3 (d), 99.7 (d), 78.0 (d), 76.4 (d), 62.9 (t), 52.9 (q), 52.7, 52.7 (t), 52.5 (d), 48.5 (t), 45.5 (t), 42.4 (t), 36.8 (t), 24.8 (d), 23.3 (q), 21.6 (q); MS m/z 459 (10), 400 (1), 330 (1), 175 (19), 91 (100); IR(CHCl3) 2940, 1740, 1672 cm$^{-1}$; Anal.

Calcd for C24H33N3O6 (459.55): C, 62.73; H, 7.24; N, 9.14. Found: C, 61.34; H, 6.82; N, 8.50.

Example 5

(2S)-2-[(1R,5S,7S)-7-(4-phenylethyl-piperazine-1-carbonyl)-2-oxo-6,8-dioxa-3-aza-bicyclo[3.2.1]oct-3-yl]-4-methyl-pentanoic acid methyl ester [compound of formula (I), where R1=—CH(Leu side chain)COOCH3, R2=H, R3 and R4=—CH2CH2N(—CH2CH2Ph)CH2CH2-]

Compound of formula (I), where R1=—CH(Leu side chain)COOCH3, R2=H, R3 and R4=—CH2CH2N(—CH2CH2Ph)CH2CH2- was prepared according to the procedure described for compound of formula (I), where R1=—CH(Leu side chain)COOCH3, R2=H, R3 and R4=—CH2(CH2)3CH2-, starting from compound of formula (VI), where R=Leu side chain, (100 mg, 0.32 mmol) and 1-phenyl-ethyl piperazine (1.2 ml, 6.3 mmol). Pure compound of formula (I), where R1=—CH(Leu side chain)COOCH3, R2=H, R3 and R4=—CH2CH2N(—CH2CH2Ph)CH2CH2- (89 mg, 59% yield) was obtained as a yellow oil.

$[\alpha]_D^{25}$ 21.3 (c 0.9, CHCl$_3$); $^1$H-NMR (CDCl3, 200 MHz): δ 7.33-7.18 (m, 5H), 5.88 (d, J=2 Hz, 1H), 5.17 (s, 1H), 5.09 (dd, J$_1$=8 Hz, J$_2$=6 Hz, 1H), 4.81 (s, 1H), 3.72 (s, 3H), 3.78-3.63 (m, 4H), 3.57 (dd, J$_1$=12 Hz, J$_2$=2 Hz, 1H), 3.18 (d, J=12 Hz, 1H), 2.88-2.80 (m, 2H), 2.70-2.58 (m, 6H), 1.78-1.70 (m, 2H), 1.53-1.25 (m, 1H), 0.98 (d, J=6 Hz, 3H), 0.94 (d, J=6 Hz, 3H); $^{13}$C-NMR (CDCl3, 200 MHz): δ 170.6 (s), 166.5 (s), 164.8 (s), 138.5 (s), 128.4 (d), 128.3 (d), 126.1 (d), 99.5 (d), 77.7 (d), 76.9 (d), 59.5 (t), 52.6 (q), 52.4, 52.2 (t), 51.9 (t), 48.2, 44.3 (t), 41.3 (t), 36.5 (t), 32.4 (t), 24.4 (d), 22.8 (q), 21.2 (q); MS m/z 414 (1), 382 (95), 56(100); IR (CHCl$_3$) 2923, 1740, 1672 cm$^{-1}$; Anal. Calcd. for C25H35N3O6 (473.57): C, 63.41; H, 7.45; N, 8.87. Found: C, 62.28; H, 7.01; N, 8.96.

Example 6

(2S)-4-Methyl-2-[(1R,5S,7S)-2-oxo-7-(piperidine-1-carbonyl)-6,8-dioxa-3-aza-bicyclo[3.2.1]oct-3-yl]-pentanoic acid (3-butylcarbamoyl-2-hydroxy-propyl)-amide [compound of formula (I), where R1=—CH(Leu side chain)COR5, R2=H, R3 and R4=—CH2CH2OCH2CH2-, R5=—NHCH2CH(OH)CH2CONHBu]

To a solution of 4-amino-3-hydroxy-butyric acid methyl ester hydrochloride salt, (37 mg, 0.22 mmol) in DCM (4 ml) were added, under a nitrogen atmosphere and at 0° C., PyBrOP (102 mg, 0.22 mmol), (2S)-4-methyl-2-[(1R,5S,7S)-2-oxo-7-(piperidine-1-carbonyl)-6,8-dioxa-3-aza-bicyclo[3.2.1]oct-3-yl]-pentanoic acid (80 mg, 0.22 mmol), previously obtained by basic ester hydrolysis of compound of formula (I), where R1=—CH(Leu side chain)COOCH3, R2=H, R3 and R4=—CH2(CH2)3CH2-, with LiOH, and DIPEA (85 μl, 0.5 mmol). The resulting solution was allowed to reach room temperature and was stirred overnight. The reaction mixture was then washed with a saturated solution of NaHCO3, aqueous 5% KHSO4, brine and dried over Na$_2$SO$_4$. After evaporation of the solvent the crude product was diluted in EtOAc and left for three hours at 4° C. in order to allow precipitation of the PyBrOP. After purification by flash chromatography, the resulting compound (40 mg, 0.08 mmol) was treated with n-butyl amine (168 μl, 1.7 mmol) in a mixture of THF (200 μl) and two drops of H2O at 50° C. for three days. Filtration of the reaction mixture on Amberlyst 15 and further purification by column chromatography (silica gel, DCM/MeOH 20:1) afforded 30 mg of compound of formula (I), where R1=—CH(Leu side chain)COR5, R2=H, R3 and R4=—CH2CH2OCH2CH2-, R5=—NHCH2CH(OH)CH2CONHBu as a colourless oil.

$^1$H-NMR (CDCl3, 200 MHz): δ 6.81-6.68 (m, 1H), 6.41-6.22 (m, 1H), 5.90, 5.86 (s, 1H, mixture of two diastereoisomers), 5.14-4.81 (m, 3H), 4.13-3.92 (m, 1H), 3.66-3.35 (m, 6H), 3.36-3.02 (m, 4H), 2.28 (d, J=5.2 Hz, 2H), 1.88-1.20 (m, 13H), 0.97-0.87 (m, 9H); $^{13}$C-NMR (CDCl3, 200 MHz): δ 171.5 (s), 170.2 (s), 168.0 (s), 164.8 (s), 99.6 (d), 77.9 (d), 67.9 (d), 54.1, 53.9 (d), 47.6 (t), 46.6 (t), 44.5 (t), 43.6 (t), 39.4 (t), 36.4 (t), 34.9 (t), 31.6 (t), 26.4 (t), 25.6 (t), 24.9 (d), 24.6 (t), 23.1 (q), 22.0 (q), 20.3 (t), 13.9 (q); MS m/z 510 (3), 309 (34), 112 (69), 84 (100).

The following examples are reported to give a non-limiting illustration of the in vitro and in vivo activity of selected compounds of the present invention.

Protease Enzyme Assay

Spectrophotometric method: protease activity of the various compounds of formula (I) was measured by a spectrophotometric assay with respect to pepstatin activity at the same concentration: each assay contained 50 μl of sample in 0.4 ml of 1% (w/v) BSA in 50 mM sodium citrate pH 3.2 and 50 μl of protease solution (1 μg/ml) After 30 min at 37° C. 1 ml 10% (w/v) trichloroacetic acid was added. The tubes were stored in ice for 30 min, and then centrifuged (3000 g) for 10 min. The absorbance of the supernatant was read at 280 nm. Control: 1% BSA in citrate buffer. One unit of the enzyme catalysed a $\Delta A_{280}$ of 1 min$^{-1}$. With the pure protease the assay was proportional to enzyme concentration over the range $\Delta A_{280}$ 0.1-0.4 and a limit detection of 1 μg (De Bernardis F., Sullivan P. A., Cassone A. *Medical Mycology* 2001, 39, 303).

TABLE 1

In vitro activity towards SAP2 of representative compounds of the present invention.
I% is the percent of inhibition with respect to pepstatin at the same concentration of 10 μm.

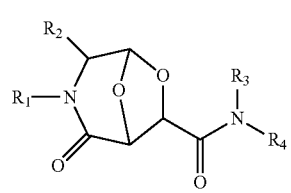

(I)

| Cpd | R1 | R2 | R3 | R4 | R5 | I% |
|---|---|---|---|---|---|---|
| 1 | —CH(Leu side chain)COR5 | H | | —CH2(CH2)3CH2— | OCH3 | 37 |
| 2 | —CH(Leu side chain)COR5 | H | | —CH2CH2OCH2CH2— | OCH3 | 32 |
| 3 | —CH(Leu side chain)COR5 | H | | —CH2(CH2)3CH2— | NHCH2CH(OH) | 22 |

TABLE 1-continued

In vitro activity towards SAP2 of representative compounds of the present invention.
1% is the percent of inhibition with respect to pepstatin at the same concentration of 10 µm.

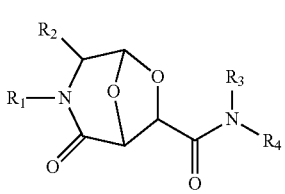

(I)

| Cpd | R1 | R2 | R3 | R4 | R5 | 1% |
|---|---|---|---|---|---|---|
| | | | | | CH2CONHBu | |
| 4 | —CH2Ph | H | H | —CH2CH2OH | — | 36 |
| 5 | —CH2Ph | H | H | —CH(Leu side chain)CH2OH | — | 41 |
| 6 | —CH2Ph | H | H | —CH2(CH2)3CH2— | — | 42 |
| 7 | —CH2Ph | H | H | —(CH2)2NCH2CH2OH(CH2)2— | — | 34 |
| 8 | —CH2Ph | H | H | —CH2CH2OCH2CH2— | — | 31 |
| 9 | —CH2Ph | H | H | —CH2CH2NC(O)OCH2CH3CH2CH2— | — | 37 |
| 10 | —CH2Ph | H | H | —(CH2)3OH | — | 12 |
| 11 | —CH2Ph | H | H | —CH(Pro side chain)CH2OH | — | 24 |
| 12 | —CH2Ph | H | H | —CH(D-Pro side chain)CH2OH | — | 17 |
| 13 | —CH2Ph | H | H | —CH(Phg side chain)CH2OH | — | 16 |
| 14 | —CH2Ph | H | H | —CH(Phe side chain)CH2OH | — | 19 |
| 15 | —CH2Ph | H | H | —CH(D-Phe side chain)CH2OH | — | 15 |
| 16 | —CH2Ph | —CH2Ph | H | —(CH2)3CH3 | — | 17 |
| 17 | —CH2Ph | —CH2Ph | H | —(CH2)5CH3 | — | 21 |
| 18 | —CH2Ph | —CH2Ph | H | —CH2CF3 | — | 17 |
| 19 | —CH2Ph | —CH2Ph | | —CH2CH2OCH2CH2— | — | 25 |
| 20 | —CH2Ph | —CH2Ph | | —CH2CH2SCH2CH2— | — | 28 |
| 21 | —CH2Ph | —CH2Ph | | —(CH2)2NCH2CH2OH(CH2)2— | — | 31 |

In Vivo Assay

Experimental vaginal infection: for the experimental vaginal infection, a previously described rat vaginal model was adopted (De Bernardis, F.; Boccanera, M.; Adriani, D.; Spreghini, E.; Santoni, G.; Cassone, A. *Infect. Immun.*, 1997, 65, 3399).

In brief, oophorectomized female Wistar rats (80-100 g; Charles River Calco, Italy) were injected subcutaneously with 0.5 mg of estradiol benzoate (Estradiolo, Amsa Farmaceutici srl, Rome, Italy). Six days after the first estradiol the animals were inoculated intravaginally with 107 yeast cells in 0.1 ml of saline solution of each *C. albicans* strain tested. The inoculum was dispensed into the vaginal cavity through a syringe equipped with a multipurpose calibrated tip (Combitip; PBI, Milan, Italy). The yeast cells had been previously grown in YPD broth (yeast extract 1%; peptone 2%; dextrose 2%) at 28° C. on a gyrator shaker (200 rpm), harvested by centrifugation (1500 g), washed, counted in a hemocytometer, and suspended to the required number in saline solution. The number of cells in the vaginal fluid was counted by culturing 100 µl samples (using a calibrated plastic loop, Disponoic, PBI, Milan, Italy) taken from each animals, on Sabouraud agar containing chloramphenicol (50 µg/ml) as previously described. The rat was considered infected when at least 1 CFU was present in the vaginal lavage, i.e. a count of >103 CFU/ml.

As a representative example for in vivo studies, one of the compounds of formula (I), as above described and hereinafter named APG12, corresponding to compound 6 of Table 1, was administered intravaginally at concentrations of 10 µM 1 h, 24 h and 48 h after intravaginal *Candida albicans* challenge with two different strains, namely SA40 and the pharmacoresistant AIDS68. Positive (pepstatin 10 µg; fluconazole 10 µg and negative (sterile saline solution) were similarly administered.

The profile of *Candida albicans* clearance in rats intravaginally treated with APG12 is similar to the acceleration observed in rats treated with the natural SAP2 inhibitor pepstatin, and in rats treated with fluconazole (Table 2 and FIG. 1). More importantly, the acceleration of *Candida albicans* clearance in the pharmacoresistant AIDS68 strain shows efficacy of both the natural SAP2 inhibitor pepstatin and of APG12, whereas the fluconazole is ineffective, showing a clearance profile similar to the untreated control (Table 3 and FIG. 2).

TABLE 2

Acceleration of *Candida* SA40 clearance in rats intravaginally treated with APG12 after challenge (1, 24, 48 hrs)

| DAYS | SA40 + APG12 | SA40 + pepstatin | SA40 |
|---|---|---|---|
| 0 | >100 | >100 | >100 |
| 1 | 70 ± 1.3 | 56.8 ± 2 | >100 |
| 2 | 57.6 ± 1.4 | 51 ± 1.2 | >100 |
| 5 | 39.2 ± 3 | 32.4 ± 2.5 | 80 ± 2.6 |
| 7 | 30.6 ± 1.8 | 28 ± 1.5 | 66 ± 2.1 |
| 14 | 14.4 ± 1.6 | 9.4 ± 1.4 | 26.2 ± 1.8 |
| 21 | 8 ± 1.5 | 5 ± 1.3 | 12.8 ± 1.2 |
| 28 | 1.2 ± 0.7 | 0 | 5.8 ± 1.6 |

All values×1000; SA40: untreated control; Starting day 1, all differences between APG12-treated and untreated control are statistically significant; (P<0.01, Mann-withney U test)

TABLE 3

Acceleration of *Candida* AIDS68 clearance in rats intravaginally treated with APG12 after challenge (1, 24, 48 hrs)

| DAYS | AIDS68 + APG12 | AIDS68 + pepstatin | AIDS68 + fluconazole | AIDS68 |
|---|---|---|---|---|
| 0  | >100 ± 0   | >100 ± 0   | >100 ± 0   | >100 ± 0   |
| 1  | 71.8 ± 1.3 | 58.4 ± 1.0 | 100 ± 0    | 100 ± 0    |
| 2  | 62.6 ± 1.5 | 52.0 ± 1.3 | 93 ± 4.3   | 100 ± 0    |
| 5  | 40.6 ± 1.4 | 37.2 ± 1.6 | 61 ± 2.5   | 71 ± 1.6   |
| 7  | 23.2 ± 1.4 | 30.0 ± 1.2 | 44 ± 2.9   | 50 ± 3.5   |
| 14 | 12.8 ± 1.2 | 19.8 ± 0.8 | 18.7 ± 3.8 | 25 ± 1.6   |
| 21 | 3.4 ± 1.7  | 3.8 ± 1.9  | 11.7 ± 0.7 | 10.7 ± 1.6 |
| 28 | 0 ± 0      | 0 ± 0      | 0 ± 0      | 7.7 ± 3    |

All values×1000; AIDS68: untreated control; Starting day 1, all differences between APG12-treated and untreated control are statistically significant; ($P<0.01$, Mann-withney U test)

The invention claimed is:

1. A compounds of formula (I)

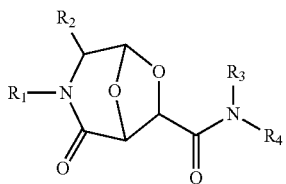

wherein:
R1 is —CH(R)COR5;
R is an α-amino acid side chain;
R2 is H, alkyl, aryl, alkylaryl;
R3 and R4 are independently selected from the group consisting of H, alkyl, alkenyl, alkynyl, cycloalkyl, alkylaryl, aryl, hydroxyalkyl, alkoxyalkyl, alkoxycarbonyl, and —CH(α-amino acid side chain)CH$_2$OH;
R3 and R4 together with the nitrogen atom to which they are connected can form a ring, selected from the group consisting of piperidine, 4-hydroxyethyl-piperazine, 4-methyl-piperazine, 4-carboethoxy-piperazine, 4-phenylethyl-piperazine, 4-benzyl-piperazine, and morpholine;
R5 is selected from the group consisting of -Oalkyl, -Oaryl, -NHalkyl, NHaryl, and amino acid;
comprising all the possible combination of stereoisomers.
the term "amino acid" includes every natural α-amino acids of the L or D series having as "side chain": —H for glycine; —CH3 for alanine; —CH(CH$_3$)$_2$ for valine; —CH$_2$CH(CH$_3$)$_2$ for leucine; —CH(CH$_3$)CH$_2$CH$_3$ for isoleucine; —CH$_2$OH for serine; —CH(OH)CH$_3$ for threonine; —CH$_2$SH for cysteine; —CH$_2$CH$_2$SCH$_3$ for methionine; —CH$_2$-(fenil) for phenylalanine; —CH$_2$-(fenil)-OH for tyrosine; —CH$_2$-(indole) for tryptophan; —CH$_2$COOH for aspartic acid; —CH$_2$C(O)(NH$_2$) for asparagine; —CH$_2$CH$_2$COOH for glutamic acid; —CH$_2$CH$_2$C(O)NH$_2$ for glutamine; —CH$_2$CH$_2$CH$_2$—N(H)C(NH$_2$)NH for arginine; —CH$_2$-(imidazole) for hystidine; —CH$_2$(CH$_2$)$_3$NH$_2$ for lysine, comprising the same side chains of amino acids bearing suitable protecting groups; and the term "amino acid" includes non natural amino acids, such as ornitine (Orn), norleucine (Nle), norvaline (NVa), β-alanine, L or D α-phenylglycine (Phg), diaminopropionic acid, diaminobutyric acid, aminohydroxybutyric acid, and other well known in the state of the art of peptide chemistry.

2. Compounds of formula (I) according to claim 1 wherein: R2 is H, benzyl, methyl, isobutyl.

3. Compounds of formula (I) according to claim 2 wherein: R is selected from the group consisting of Gly, Leu, Val, Ile, Ala, Phe, Phg, Nle, and Nva.

4. Compounds of formula (I) according to claim 3 wherein:
R3 and R4 are independently selected from the group consisting of H, hydroxyethyl, propargyl, and —CH(Leu side chain)CH$_2$OH;
R3 and R4 together with the nitrogen atom to which they are connected can form a ring, selected from the group consisting of piperidine, 4-hydroxyethyl-piperazine, 4-methyl-piperazine, 4-carboethoxy-piperazine, 4-phenylethyl-piperazine, 4-benzyl-piperazine, and morpholine.

5. Compounds of formula (I) according to claim 4 wherein:
R3 is H and R4 is selected from the group consisting of H, hydroxyethyl, propargyl, and —CH(Leu side chain) CH$_2$OH; or
R3 and R4 together with the nitrogen atom to which they are connected can form a ring, selected from the group consisting of piperidine, 4-hydroxyethyl-piperazine, and 4-carboethoxy-piperazine.

6. Compounds of formula (I) according to claim 5 wherein: R is Leu side chain.

7. A compound of formula (I) according to claim 1 for use as a medicament.

8. A method of treating infectious diseases in a patient in need thereof wherein a compound of formula (I) is administered,
wherein:

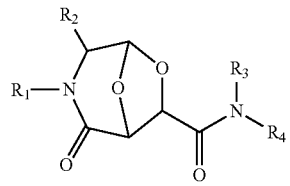

R1 is selected from the group consisting of benzyl, —CH(R)COR5 wherein said R is a α-amino acid is selected from the group consisting of Gly, Leu, Val, Ile, Ala, Phe, Phg, Nle, and Nva,
R2 is selected from the group of H, benzyl, methyl, and isobutyl;
R3 and R4 are independently selected from the group consisting of H, hydroxyethyl, propargyl, and —CH(Leu side chain)CH$_2$OH;
R3 and R4 together with the nitrogen atom they are bonded to can form a cyclic compound, selected from the group consisting of piperidine, 4-hydroxy-piperazine, and 4-carboethoxy-piperazine,
comprising all the possible combination of stereoisomers; wherein the infectious diseases are associated with microbial pathogens expressing aspartyl-protease activity.

9. The method according to claim 8 wherein the infectious diseases is associated with pathogens selected from the group consisting of *Candida albicans*, HIV, HTVL, and *Plasmodium falciparum*.

10. The method according to claim 9 for the treatment of drug resistant infectious diseases associated with *Candida albicans*.

11. A pharmaceutical composition containing at least one compound of formula (I) according to claim 1, and at least another pharmaceutically acceptable ingredient, carrier or diluent.

* * * * *